United States Patent [19]

Gijselhart et al.

[11] Patent Number: 4,909,786
[45] Date of Patent: Mar. 20, 1990

[54] APPARATUS FOR CONTROLLING THE FLOW OF AN INFUSION FLUID IN AN INFUSION SYSTEM

[75] Inventors: Paulus H. P. M. Gijselhart, Best; Adriaan van der Wouden, Zundert, both of Netherlands

[73] Assignee: W. M. H. Kerbosch B.V., Leersum, Netherlands

[21] Appl. No.: 277,961

[22] Filed: Nov. 30, 1988

[30] Foreign Application Priority Data

Dec. 17, 1987 [NL] Netherlands .......................... 8703055
Sep. 16, 1988 [NL] Netherlands .......................... 8802307

[51] Int. Cl.⁴ .............................................. A61M 5/00
[52] U.S. Cl. ...................................... 604/65; 604/253; 128/DIG. 13
[58] Field of Search ...................................... 604/65–67, 604/251, 253, 250; 128/DIG. 13, DIG. 12

[56] References Cited

U.S. PATENT DOCUMENTS

| | | | |
|---|---|---|---|
| 4,443,216 | 4/1984 | Chappell | 604/67 |
| 4,507,112 | 3/1985 | Hiller et al. | 604/65 |
| 4,525,163 | 6/1985 | Slavik et al. | 604/65 |
| 4,820,268 | 4/1989 | Kawamura et al. | 604/67 |

Primary Examiner—Stephen C. Pellegrino
Attorney, Agent, or Firm—Lorusso & Loud

[57] ABSTRACT

An apparatus for controlling the flow of an infusion fluid in an infusion system with a drip chamber and a deformable tube, is provided with a sensor for detecting the drops of infusion fluid falling in the drip chamber, means for seting a desired flow rate, pinch clamp means for pinching off the deformable tube and a processing unit for controlling the pinch clamp means is dependence of the set desired flow rate and the signal of the sensor. The pinch clamp means is movable with a variable speed between a rest position in which the tube is fully released, and a closed position in which the tube is fully closed. The speed in a controlling range preceding the closed position is substantially lower than the speed adjacent the rest position.

8 Claims, 3 Drawing Sheets

APPARATUS FOR CONTROLLING THE FLOW OF AN INFUSION FLUID IN AN INFUSION SYSTEM

BACKGROUND OF THE INVENTION

The invention relates to an apparatus for controlling the flow of an infusion fluid in an infusion system with a drip chamber and a deformable tube, said apparatus comprising a sensor for detecting the drops of infusion fluid falling in the drip chamber, means for setting a desired flow rate, pinch clamp means for pinching off the deformable tube and a processing unit for controlling the pinch clamp means in dependence on the set desired flow rate and the signal of the sensor.

Such apparatus are known in various embodiments and are for example disclosed in U.S. Pat. Nos. 4,507,112 and 4,525,163. In such apparatus the accuracy of controlling the pinch clamp means is of great importance. The embodiment described in U.S. Pat. No. 4,507,112 appears not to have a satisfactory operation in practice. The apparatus disclosed in U.S. Pat. No. 4,525,163 uses a drip chamber formed in a special manner in which a closing element is provided.

The invention aims to provide an apparatus of the above-mentioned type, by which the flow rate of an infusion fluid can be controlled in a very accurate manner in an infusion system equipped with a conventional drip chamber.

SUMMARY OF THE INVENTION

To this end the apparatus according to the invention is characterized in that said pinch clamp means is movable with a variable speed between a rest position in which the tube is fully released, and a closed position in which the tube is fully closed wherein the speed in a controlling range preceding the closed position is substantially lower than the speed adjacent the rest position.

In this manner it is obtained that during movement of the pinch clamp means along the controlling range, an accurate adjustment of the flow rate is possible, whereas for movement of the pinch clamp means from/towards the rest position a relatively high speed is possible so that the tube can be fully opened or closed quickly.

According to an embodiment of the invention the pinch clamp means is drivable by an electric motor, wherein the processing unit provides current pulses with a variable length to the electric motor.

Preferably the pinch clamp means comprises a movable slide drivable through a rotatable disc coupled to the slide by an excentric pin. Thereby the desired variation of the speed is obtained in a simple manner, wherein moreover the force which can be exerted by the pinch clamp means in the controlling range, is increased.

Because the sensor detects drops whereas the user wants to have information on the flow rate in volume per unit of time, according to a favorable embodiment of the invention a reference drop volume is stored in a memory, wherein the processing unit is adapted to compute the flow rate in volume perunit of time from the drops detected by the sensor by means of a correction factor for the infusion fluid to be used which can be stored in the memory. Thereby the flow rate can be shown on a display to be driven by the processing unit in drops and volume per unit of time, respectively at a minimum memory storage space.

In this case it can be an advantage if during delivery of the infusion fluid any possible deviations of the desired flow rate with corresponding times are stored in the memory together with the time of beginning and end of the fluid delivery. When the processing unit does not succeed to correct the deviation by controlling the pinch clamp means an alarm device will be energized and the pinch clamp means will be moved to the closed position because a situation dangerous for the patient may exist.

For recording the data the apparatus according to the invention is coupled through the sensor to a central computer for receiving a correction factor for the infusion fluid to be used and possibly an amount of infusion fluid to be delivered on the one side and for transmitting the data stored in the memory on the course of the delivery of an amount of infusion fluid on the other side. Thereby the possibility is obtained to provide a historical report on the fluid delivery in a simple manner. The central computer may for example comprise a program for printing a graphic representation of the fluid delivery in time on the basis of the provided data.

The invention will be further explained by reference to the drawings in which an embodiment is shown.

DETAILED DESCRIPTION OF PREFERRED EMBODIMENTS

Figure 2:
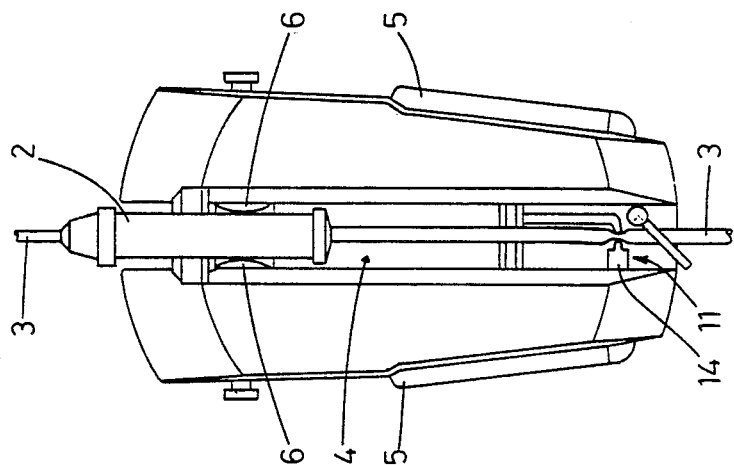
FIG. 2 is a back view of the apparatus of FIG. 1, in which the drip chamber and a part of the infusion tube of an infusion system are shown.
Figure 1:
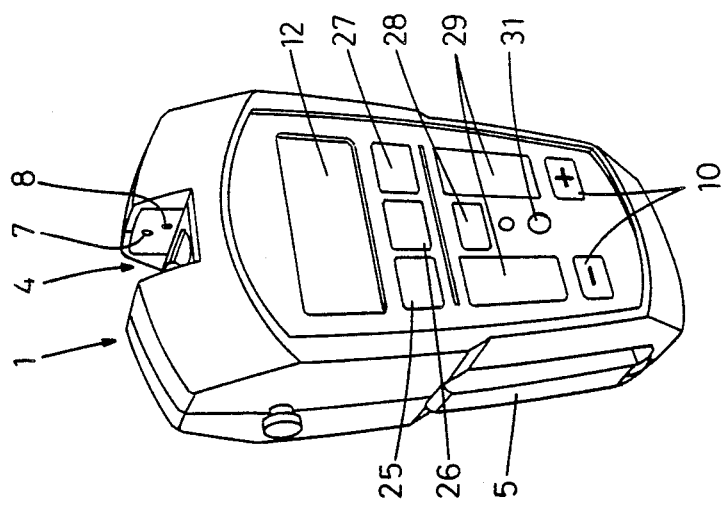
FIG. 1 is a perspective view of an embodiment of the apparatus according to the invention.

Referring to FIGS. 1 and 2 there is shown an apparatus 1 for controlling the flow of an infusion fluid in an infusion system of which FIG. 2 shows a drip chamber 2 and a deformable tube 3. At the back side of the apparatus 1 there is a receiving space 4 in which the drip chamber 2 can be disposed. To this end two actuating elements 5 are to be pressed, whereby clamping elements 6 will withdraw from the receiving space 4, so that the drip chamber 2 can be located there.

At the upper side of the receiving space 4 two sensors are provided for detecting the drops falling into the drip chamber 2, said sensors each consisting of an infrared transmitter 7 and receiver 8. In FIG. 1 only the transmitter 7 and receiver 8 of both sensors on one side are visible. In the block diagram of FIG. 5 to be discussed hereafter, only one transmitter/receiver pair is shown. The transmitter/receiver pairs 7, 8 are disposed in displaced locations whereby falling drops can be detected in a relatively large area and no drops are missed during movements of the drip chamber 2.

Figure 5:
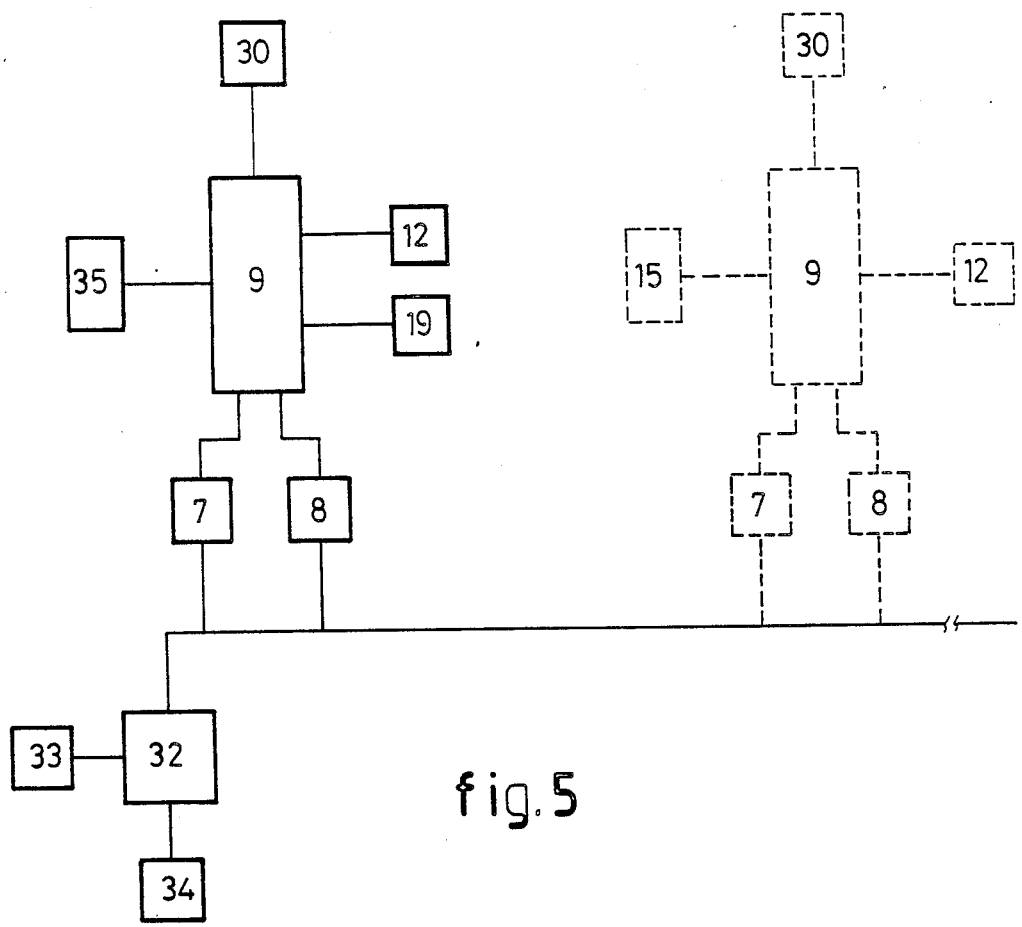
FIG. 5 is a block diagram of the apparatus according to FIG. 1.

The transmitter/receiver pairs 7, 8 are connected to a processing unit indicated by 9 in the block diagram of FIG. 5. A the front side of the apparatus 1 two setting buttons 10 are provided for setting a desired flow rate. Pressing the left setting button 10 results in a decrease of the flow rate, pressing the right setting button 10 results in an increase of the flow rate. To this end the signals of the setting buttons 10 are supplied to the processing unit 9 which in response to these signals controls a pinch clamp means 11 for pinching off the tube 3 in such manner that the actual flow rate as determined by means of the signals of the transmitter/receiver pairs 7, 8 will be equal to the desired flow rate. The processing unit 9 shows the flow rate on a display 12.

Figure 3:
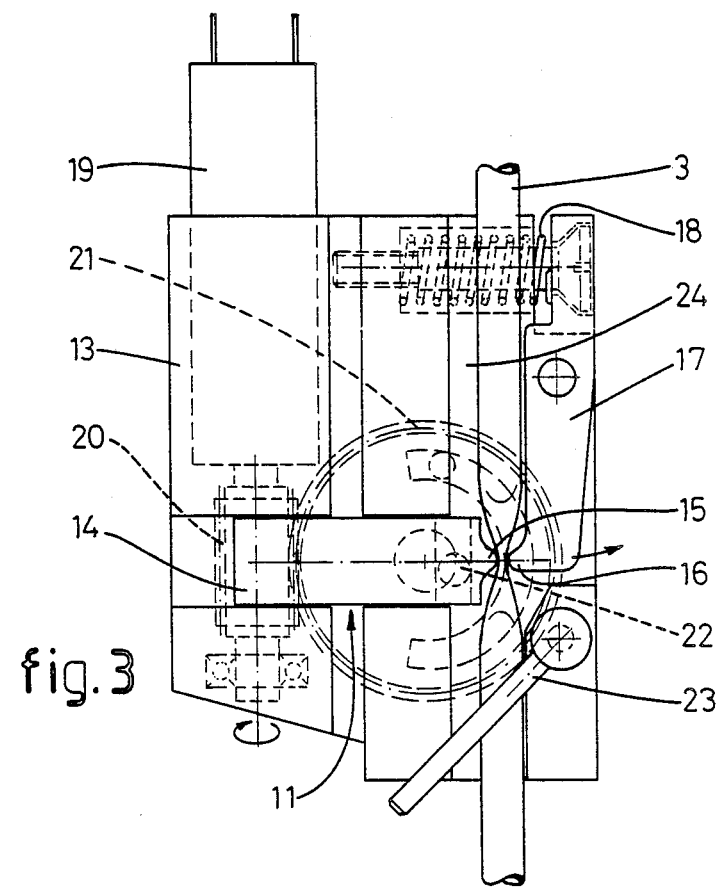
FIG. 3 shows a part of the apparatus of FIG. 1 on a larger scale, wherein the pinch clamp means is in the controlling range preceding the closed position.
Figure 4:
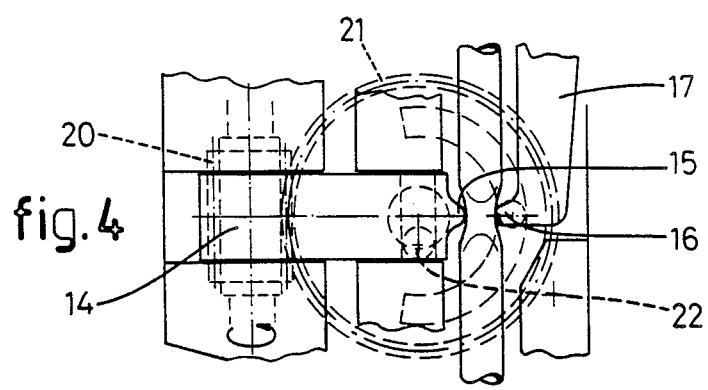
FIG. 4 shows a part corresponding to FIG. 3, in which the pinch clamp means is moved in the direction of the rest position.

The pinch clamp means 11 is further shown in FIGS. 3 and 4 together with an associated mounting block 13. The pinch clamp means 11 is formed by a slide 14 with a projection 15 movable in the mounting block 13, which projection 15 cooperates with a counter projection 16 of an arm 17 which is rotatable around a shaft against the action of a spring 18. In FIG. 3 the slide 14 is in a controlling range preceding a closed position, in which controlling range the slide 14 is movable by an electric motor 19 with a very low speed in the direction of the counter projection 16. Further the processing unit 9 controls the electric motor 19 with relatively short current pulses with a duration of 7-10 ms for example. Thereby an accurate control of the flow rate through the infusion tube 3 is possible in the controlling range. In FIG. 4 the slide 14 is substantially in a rest position, in which the tube 3 is substantially released so that the tube may be removed from the apparatus. In the movement range near this rest position the slide 14 is moved relatively quickly so that the slide will be moved quickly to the controlling range. In this movement range of the slide 14 adjacent the rest position, the processing unit 9 controls the electric motor 19 with current pulses of a longer duration, for example 50 ms decreasing to 10 ms when approaching the controlling range.

In the described apparatus the electric motor 19 is further coupled to the slide 14 through a screw wheel 20 and a gear wheel 21. The rotation axis of the gear wheel 21 lies substantially on the centre line of the slide 14. The gear 21 is coupled to the slide 14 through an excentric pin 22 which engages a slot of the slide 14. As appears from a comparison of FIGS. 3 and 4, this coupling construction results in that the slide starting from the rest position of FIG. 4 with an equal angular rotation of the gear 21 will be moved initially with a high speed and in the controlling range of FIG. 3 will be moved with a lower speed, wherein in the controlling range the force which can be exerted by the slide 14, is especially high. In a prototype of the described apparatus in this manner a step size for the movement of the slide 14 of approximately 0.005 mm was obtained in the control range.

Because the counter projection 16 is movable against the action of the spring 18 when reaching the closed position of the slide 14, a damage of the tube 3 by too high forces is prevented.

As appears from FIGS. 2 and 3, a locking element 23 is mounted on the mounting block 13 for holding the tube 3 in a receiving slot 24 formed in the mounting block 13 when the locking element 23 is rotated into the shown position. For removing the tube 3 from the receiving slot 24 the locking element 23 can be pivoted away.

According to FIG. 1 three operating buttons 25-27 are provided below the display 12. By means of the button 25 the electric motor 19 can be operated for moving the slide 14 to the rest position or the closed position, respectively. When a drip chamber 2 with infusion tube 3 is arranged in the apparatus, the slide 14 can be moved into the closed position by means o this button 25. Subsequently the control operation of the apparatus 1 can be started o stopped respectively by means of the button 27. By means of the button 26 a predetermined minimum flow rate can be set which is such that there will be no coagulation phenomena or the like in the blood vessel in which the infusion needle is inserted. Below button 26 there is a button 28 by which can be switched between drips of a normal size or a micro size. Finally two large safety buttons 29 are provided which have the same function and one of which has to be pressed to enable the operation of one of the other buttons. Thereby an accidental operation of the buttons 10, 25-28 is prevented.

As the transmitter/receiver pairs 7, 8 detect drops and one wants to have also the flow rate in volume per unit of time, a reference drop volume is stored in the memory 30 (see FIG. 5), so that the processing unit can convert the drops into a volume. The apparatus also contains a real time clock, so that the processing unit 9 can compute the flow rate and can show the same on the display 12 in volume and drops per unit of time, respectively.

In order to provide the possibility of an accurate determination of the volume, the apparatus 1 has to take into account the type of infusion fluid to be delivered, because the volume of a drop depends on the fluid characteristics. To this end a correction factor can be stored in the memory 30, by which the reference drop volume has to be multiplied for obtaining the correct volume of the fluid type used.

During delivery of an infusion fluid the apparatus stores several important data in he memory 30, such as the beginning time and end time of the fluid delivery. During delivery of the infusion fluid the processing unit 9 controls the slide 14 in such a manner that the flow rate is substantially equal to the flow rate set by means of the setting buttons 10. At the front of the apparatus a light emitting diode 31 is provided which lights up at every detected drop so that the user of the apparatus 1 may check the correct operation. When the processing unit 9 determines that the deviation between the set desired flow rate and the detected flow rate exceeds a predetermined threshold level, the slide 14 is controlled for eliminating this deviation. Further the time and value of the deviation are recorded in the memory 30. When it appears that the deviation cannot be corrected, the tube 3 is fully closed and a visual alarm indication is provided. It is for example possible that the processing unit 9 shows an alarm message on the display 12.

It is also possible to store a desired amount of infusion fluid to be delivered in the memory 30, so that the processing unit 9 can stop the delivery of the fluid automatically as soon as the desired total amount is reached.

For the input of the above indicated correction factor and the desired amount of fluid to be delivered, the apparatus 1 can be coupled with a central computer, of which a central processing unit 32, a keyboard 33 and a memory 34 are shown in the block diagram of FIG. 5. The keyboard of the apparatus 1 is indicated in FIG. 5 by a single block 35. As is rather schematically shown in FIG. 5, the coupling with the central computer 32-34 takes place through a transmitter/receiver pair 7, 8 so that no further auxiliary means are necessary for making the coupling with the central computer. In this manner information on the correction factor for the drop volume of the type infusion fluid to be delivered together with for example the desired amount of fluid to be delivered, is provided to the apparatus 1. On the other hand the historical data of the course of the delivery of the infusion fluid to the patient can be transmitted from the apparatus to the central computer. The central computer can make a graphic representation of this course as function of the time from this provided data.

As indicated by a dashed line in FIG. 5, more apparatus of the described type can be coupled to the central computer 32–34.

The invention is not restricted to the above-described embodiment, which can be varied in a number of ways within the scope of the invention.

We claim:

1. Apparatus for controlling the flow of an infusion fluid in an infusion system with a drip chamber to which is connected a deformable tube, said apparatus comprising:
   - a sensor positioned adjacent said drip chamber for detecting the drops of infusion fluid falling in the drip chamber, said sensor providing a signal for each drop;
   - means for selecting a desired fow rate;
   - pinch clamp means for pinching off the deformable tube reciprocally supported adjacent said deformable tube; and
   - a processing unit for controlling the pinch clamp means in dependence on the selected desired flow rate and the signal of the sensor, wherein said pinch clamp means is movable with a variable speed between a rest position in which the deformable tube is fully released, and a closed position in which the deformable tube is fully closed wherein the speed in a controlling range preceding the closed position is substantially lower than the speed adjacent the rest position.

2. Apparatus according to claim 1, wherein the pinch clamp means is drivable by an electric motor and wherein the processing unit provides current pulses with a variable length to the electric motor.

3. Apparatus according to claim 2, wherein the pinch clamp means comprises ammovable slide drivable through a rotatable disc coupled to the slide by an excentric pin.

4. Apparatus according to claim 1, wherein the pinch clamp means cooperates with a counter projection which is movable against the action of a spring.

5. Apparatus according to claim 1, wherein the pinch clamp means is mounted in a mounting block in which a receiving slot is formed for the tube, wherein a locking element is provided for holding the tube in the receiving slot.

6. Apparatus according to claim 1, wherein a reference drop volume is stored in a memory, wherein the processing unit is adapted to compute the flow rate in volume per unit of time from the drops detected by the sensor by means of a correction factor for the infusion fluid to be used which can be stored in the memory.

7. Apparatus according to claim 6, wherein during delivery of the infusion fluid any possible deviations of the desired flow rate with corresponding times are stored in the memory together with the time of beginning and end of the fluid delivery.

8. Apparatus according to claim 7, wherein the apparatus can be coupled through the sensor to a central computer for receiving a correction factor for the infusion fluid to be used and possibly an amount of infusion fluid to be delivered on the one side and for transmitting the data stored in the memory on the course of the delivery of an amount of infusion fluid on the other side.

* * * * *